United States Patent [19]

Becher et al.

[11] 4,275,077

[45] Jun. 23, 1981

[54] INSECTICIDAL ACYL UREA DERIVATIVES

[75] Inventors: Heinz-Manfred Becher, Bingen; Richard Sehring, Ingelheim am Rhein; Walter Wirtz, Darmstadt; Ricarda Prokic-Immel, Mainz, all of Fed. Rep. of Germany

[73] Assignee: Celamerck GmbH & Co. KG, Ingelheim am Rhein, Fed. Rep. of Germany

[21] Appl. No.: 110,375

[22] Filed: Jan. 8, 1980

[30] Foreign Application Priority Data

Jan. 15, 1979 [DE] Fed. Rep. of Germany ....... 2901334
Jul. 5, 1979 [DE] Fed. Rep. of Germany ....... 2927123

[51] Int. Cl.³ ...................... A01N 9/20; C07C 127/22
[52] U.S. Cl. ......................................... 424/322; 564/44
[58] Field of Search .................... 260/553 E; 424/322; 564/44

[56] References Cited

U.S. PATENT DOCUMENTS

| 3,933,908 | 1/1976 | Wellinga et al. ................. 260/553 E |
| 3,992,553 | 11/1976 | Sirrenberg et al. .......... 260/553 E X |
| 4,005,223 | 1/1977 | Sirrenberg et al. .......... 260/553 E X |
| 4,041,177 | 8/1977 | Sirrenberg et al. .......... 260/553 E X |
| 4,068,002 | 1/1978 | Sirrenberg et al. .................. 424/322 |
| 4,089,975 | 5/1978 | Wade et al. ........................... 424/322 |
| 4,162,330 | 7/1979 | Ehrenfreund ....................... 424/322 |
| 4,170,657 | 10/1979 | Rigterink ............................. 424/322 |

FOREIGN PATENT DOCUMENTS 2601780 7/1977 Fed. Rep. of Germany ....... 260/553 E

OTHER PUBLICATIONS

Wellinga et al., CA 79:88264(d), 1973.

*Primary Examiner*—Thomas A. Waltz
*Attorney, Agent, or Firm*—Hammond & Littell, Weissenberger & Muserlian

[57] ABSTRACT

This invention is directed to novel urea derivatives of the general formula $$A-\underset{Z}{\underset{|}{\bigcirc}}-NH-CO-NH-CO-\underset{Z'}{\underset{|}{\bigcirc}}-Z'' \quad (I)$$

wherein
A represents one of the groups (IIa) naphthyl-S—,
(IIb) (methylphenyl)-S— OR
(IIc) dibenzodioxin-type structure with X and Y substituents and —O—;

X and Y, which may be identical to or different from each other, each represent hydrogen, chlorine or bromine;
Z represents hydrogen or chlorine;
Z' represents chlorine or fluorine; and
Z" represents hydrogen, chlorine, or fluorine.

The invention is also directed to the production of compounds of Formula I, their use as pesticides, and pesticidal agents comprising the novel compounds as active substances.

8 Claims, No Drawings

INSECTICIDAL ACYL UREA DERIVATIVES

This invention is directed to novel urea derivatives of the general formula $$A-\underset{Z}{\underset{|}{\bigcirc}}-NH-CO-NH-CO-\underset{Z'}{\underset{|}{\overset{Z''}{\bigcirc}}} \quad (I)$$

wherein
A represents one of the groups $$\underset{(IIa)}{\bigcirc\!\bigcirc-S-}, \quad \underset{(IIb)}{\overset{CH_3}{\bigcirc}-S-} \quad OR$$

$$\underset{(IIc)}{\overset{X}{\underset{Y}{\bigcirc\!\bigcirc}}-O-};$$

X and Y, which may be identical to or different from each other, each represent hydrogen, chlorine or bromine;
Z represents hydrogen or chlorine;
Z' represents chlorine or fluorine; and
Z" represents hydrogen, chlorine, or fluorine.

Furthermore, this invention is directed to the production of compounds of Formula I, their use as pesticides, and pesticidal agents comprising the novel compounds as active substances.

The compounds of Formula I are obtained according to methods known per se:

Method 1.
By reacting an aniline of formula $$A-\underset{Z}{\underset{|}{\bigcirc}}-NH_2 \quad (III)$$

wherein A and Z are as defined above, with a benzoyl isocyanate of formula $$OCN-CO-\underset{Z'}{\underset{|}{\overset{Z''}{\bigcirc}}} \quad (IV)$$

wherein Z' and Z" are as defined above.
Method 2.

By reacting a benzamide of formula $$H_2N-CO-\underset{Z'}{\underset{|}{\overset{Z''}{\bigcirc}}} \quad (V)$$

wherein Z' and Z" are as defined above, with an isocyanate of formula $$A-\underset{Z}{\underset{|}{\bigcirc}}-NCO \quad (VI)$$

wherein A and Z are as defined above.
Method 3.

By reacting an aniline of Formula III with a benzoylurethane of formula $$RO-CO-NH-CO-\underset{Z'}{\underset{|}{\overset{Z''}{\bigcirc}}} \quad (VII)$$

wherein R represents an optionally substituted lower to middle alkyl group and Z' and Z" have the above meanings.

The reaction according to Method 1 or 2 is effected at temperatures between room temperature and the boiling temperatures of the reaction mixture within an inert solvent, for example, an aromatic hydrocarbon, such as toluene, xylene, or chlorobenzene, pyridine, an ether such as dioxan, or tetrahydrofuran, optionally in the presence of a tertiary aromatic base (triethylamine, pyridine). It is advantageous to use catalyst in quantities up to approximately 30% by weight of the isocyanate.

For the reaction of the urethanes according to Method 3, temperatures between 60° C. and the boiling temperature of the reaction mixture are chosen. Suitable solvents include aromatic hydrocarbons, such as toluene, xylene, and chlorobenzene.

The starting materials may be obtained according to conventional methods. Thus, the anilines of Formula III may be obtained from an alkali salt of an α- or β-naphthol of the formula $$\underset{Y}{\overset{X}{\bigcirc\!\bigcirc}}-OH \quad (VIII)$$

by reaction with the nitro compound of formula

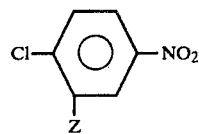

and reduction of the originated ether of formula

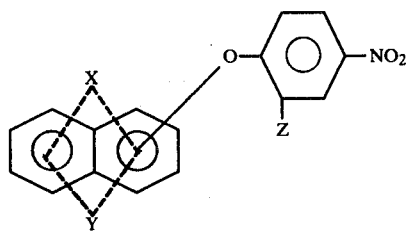

It is also possible to subsequently introduce the halogen atoms into the corresponding starting materials of Formula X (wherein X and/or Y=H).

The isocyanate VI may be obtained from the hydrochloride of the aniline III in the conventional manner known to the art.

The urethane of Formula VII can be prepared by reacting the benzamide of formula

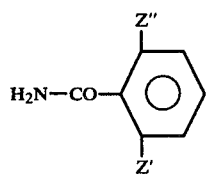

with a corresponding chloroformate.

The novel compounds are highly effective insecticides. They are especially suitable for the control of gnats, caterpillars, bugs, and bug larvae.

A preferred embodiment of the invention comprises compounds of the Formula I wherein A represents a group of the Formula IIc. More specifically, the preferred embodiment comprises compounds of the formula

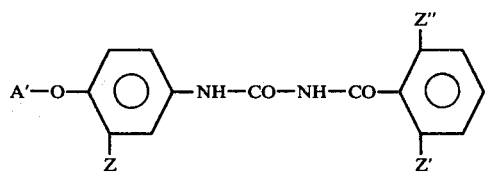

wherein A' is an α-naphthyl radical or a radical of the formula

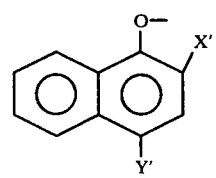

wherein one of X' and Y' is chlorine and the other is halogen, or both are hydrogen, with the provisos that (1) when A' is the radical of Formula XII, Z, Z', and Z" have the relationship

| Z  | Z" | Z' |
|----|----|----|
| H  | Cl | Cl |
| Cl | F  | F  |
| H  | F  | F  |
| H  | F  | Cl |
| Cl | F  | Cl |
| H  | H  | Cl | and (2) when A' is an β-naphthyl radical, Z, Z' and Z" have the relationship

| Z  | Z' | Z" |
|----|----|----|
| H  | Cl | Cl |
| H  | F  | F  |
| H  | F  | Cl |
| Cl | F  | F  |

When the compounds according to the invention are to be used as pesticidal agents, the compounds are processed with the usual excipients and/or carriers to form conventional formulations, such as, for example, emulsion concentrates, suspension powders, or dusts. The compounds are used in the form of sprays and dusts with active substance concentrations of from about 0.0025 to 2% by weight, and in the form of ULV-formulations also with higher concentrations of active substance (up to about 90% by weight). The dosage per hectar amounts to from about 0.05 to 0.5 kg of active substance plus carrier.

Formulation Example:
Suspension Powder (Quantities indicated in % by weight)
25% of active substance according to invention
55% of kaolin
10% of colloidal silicic acid
9% of lignine sulfonate (dispersing agent)
1% of sodium tetrapropylene benzene sulfonate (wetting agent).

The components are processed to a suspension powder as usual (particle size <4µ). For application, a spray mixture containing water can be prepared by incorporating into the water from about 0.0025 to 0.025% by weight, based on the weight of the total spray mixture, of the formulation in suspension form.

The superior effect of the compounds according to the invention is demonstrated, for example, by comparison with the commercial product of the formula

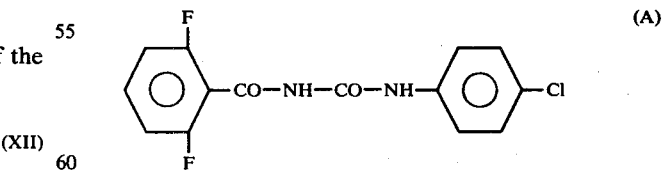

(difluorobenzurone) with the compounds according to the invention.

The values set forth in the table below were determined by a green-house test, whereby the sprays were prepared from a 0.5% solution of the active substances in acetone by dilution with a corresponding quantity of water. The test objects were the following pests:

(a) Larvae aedes aegyptii (4 days old)
(b) Caterpillars spodoptere littoralis L$_3$
(c) Bug larvae epilachna varivestis L$_3$ For pests (a) and (b) the evaluation was effected after 3 days, for pest (c) after 6 days. The results are set forth in the table below.

Active Substances:

B: N-[4-(α-naphthoxy)-phenyl]-N'-(2-chlorobenzoyl)-urea

C: N-[4-(α-naphthoxy)-3-chlorophenyl]-N'-(2,6-difluorobenzoyl)-urea

D: N-[4-(β-naphthoxy)-phenyl]-N'-(2,6-dichlorobenzoyl)-urea

E: N-[4-(α-naphthoxy)-phenyl]-N'-(2-chloro-6-fluorobenzoyl)-urea

F: N-[4-(β-naphthoxy)-phenyl]-N'-(2-chloro-6-fluorobenzoyl)-urea

G: N-[4-(α-naphthoxy)-3-chlorophenyl]-N'-(2-chloro-6-fluorobenzoyl)-urea

TABLE I

| Active Substance | A. aegyptii LD$_{95}$[ppm] | S. littoralis LD$_{95}$[ppm] | E. varivestis LD$_{95}$[ppm] |
| --- | --- | --- | --- |
| A* | 0.0031 | 3.6 | 15.0 |
| B | 0.0044 | 0.38 | — |
| C | 0.00037 | — | 8.8 |
| D | — | 0.9 | 10.5 |
| E | 0.00044 | 0.36 | 7.2 |
| F | 0.0035 | 0.30 | 7.0 |
| G | 0.00094 | 1.7 | 9.0 |

*Comparison

A further comparison was performed between the comparison compound of Formula A and H: N-(4-naphthylmercaptohphenyl)-N'-(2,6-dichlorobenzoyl)-urea I: N-(4-tolylmercaptophenyl)-N'-(2,6-dichlorobenzoyl)-urea.

Green house test: 0.5% solution of the active substance in acetone, diluted with water to 5 ppm (Test 1) or 2 ppm (Test 2).

Test 1.

Prodenia caterpillars, % of activity with control after 3 days:

A: 64%
H: 100%

Test 2:

Epilachna larvae, % of activity with control after 6 days:

A: 67%
I: 96%.

Production of Starting Materials

A. Nitro Compounds

EXAMPLE 1

4-(α-naphthoxy)-3-chloro-nitrobenzene

To a solution of 144 g (1 mol) of α-naphthol in 1 liter of xylene were added 65 g (1 mol) of finely powdered 88% potassium hydroxide. The mixture thus obtained was boiled under N$_2$-atmosphere in an apparatus equipped with an effective water trap under constant stirring until no water was separating any more and the head temperature had risen to 137° C. Then, 500 ml of dimethylformamide were added, The solution thus obtained was boiled for a further two hours under nitrogen in the apparatus equippped with an effective water trap; then, 500 ml of solvent were distilled therefrom. The residue was allowed to cool off under nitrogen to 100° C., and 211 g (1 mol) of 3,4-dichloronitrobenzene and 1 g of copper powder were added. Then it was refluxed under nitrogen while stirring for 8 hours (approx. 140° C. bottom temperature). Afterwards it was allowed to cool off to ~50° C., approx. 30 g of kieselguhr were added, the mixture thus obtained was stirred, and the undissolved substance was removed by suction filtration and washed with xylene. The filtrate united with the wash liquid was evaporated in vacuo to dryness. The residue was dissolved in warm toluene. The obtained solution was extracted thrice with separate portions of 500 ml of 1 N sodium hydroxide solution and, subsequently, twice with separate portions of 500 ml of water. Then, the toluene phase was evaporated to dryness in vacuo (crude yield: 290 g, 96% of theory). The residue was stirred with 1.7 liter of gasoline (boiling range 80°–110° C.) at approx. 85° C. Most of the crude product dissolved; some resin remain undissolved. The solution decanted therefrom was allowed to cool off slowly. First, the product precipitated oily; however, by trituration at approx. 50° C., crystals were obtained. Then it was cooled for several hours to 5° C. and the crystalline product was removed by suction filtration.

Yield: 272 g (0.907 mol), 90.7% of theory.
M.p. 78°–80° C.

EXAMPLE 2

4-(α-naphthoxy)-nitrobenzene

The method of Example 1 was followed, with the exception that, instead of the 3,4-dichloro-nitrobenzene, the same molar quantity of p-chloronitrobenzene was used.

Yield: >90% of theory.
M.p. 138°–140° C.

EXAMPLE 3

4-(β-naphthoxy)-3-chloro-nitrobenzene

The method of Example 1 was followed, with the exception that purification by means of treating with gasoline was not employed. Also, instead of the α-naphthol, β-naphthol was used.

Yield: practically quantitative.

EXAMPLE 4

4-(β-naphthoxy)-nitrobenzene

The procedure of Example 3 was used. Instead of the 3,4-dichloronitrobenzene, the same molar quantity of p-chloronitrobenzene was used.

Yield: practically quantitative.

EXAMPLE 5

4-(1-chloro-naphthoxy<2>)-3-chloro-nitrobenzene

The procedure of Example 1 was followed. Instead of the α-naphthol, the same molar quantity of 1-chloro-naphthol-(2) was used.

Yield: 79% of theory, m.p. 117°–120° C.

EXAMPLE 6

4-(1-chloro-naphthoxy<2>)-nitrobenzene

The procedure of Example 1 was followed. Instead of α-naphthol, the same molar quantity of 1-chloro-naphthol-(2) was used, and instead of the 3,4-dichloronitrobenzene, the same molar quantity of p-chloronitrobenzene was used.

Yield: 86% of theory.
M.p. 107°–109° C.

EXAMPLE 7

Production of 4-(chloronaphthoxy<1>)-3-chloro-nitrobenzene by chlorinating 4-(α-naphthoxy)-3-chloro-nitrobenzene An amount of 75 g (0.25 mol) of 4-(α-naphthoxy)-3-chloro-nitrobenzene was dissolved hot in 1 liter of glacial acetic acid. Then some benzoylperoxide and 40 g (0.30 mol) of sulfuryl chloride were added. The mixture thus obtained was refluxed for four hours. Then, it was evaporated to dryness in vacuo. The residue was dissolved in toluene, and the solution was extracted several times with water. Subsequently, the toluene phase was evaporated in vacuo to the residue.

Crude yield: 80.5 g (0.24 mol); 96% of theory.

Recrystallization of the crude product that turned crystalline from isopropyl alcohol or from ethylacetate.

Yield after recrystallizing once from ethylacetate: 54.3 g (0.16 mol, 65% of theory).

M.p. 156°–158° C.

EXAMPLE 8

Production of 4-(chloronaphthoxy<1>)-nitrobenzene by chlorinating 4-(α-naphthoxy)-nitrobenzene The procedure of Example 7 was followed. Instead of 4-(α-naphthoxy)-3-chloro-nitrobenzene, the same molar quantity of 4-(α-naphthoxy)-nitrobenzene was used. Crude yield: 97% of theory. Recrystallization of the crude product that turned crystalline from di-isopropyl ether.

Yield after recrystallizing once: 67% of theory, m.p. 63°–64° C.

Probably a mixture of two isomers was present. (Cl in 2- or 4-position of the naphthalene group).

EXAMPLE 9

Production of 4-(chloronaphthoxy<2>)-3-chloro-nitrobenzene by chlorinating 4-(β-naphthoxy)-3-chloro-nitrobenzene The procedure of Example 7 was followed. Instead of 4-(α-naphthoxy)-3-chloro-nitrobenzene, the same quantity of 4-(β-naphthoxy)-3-chloro-nitrobenzene was used.

Crude yield: 97% of theory.

Recrystallization of the crude product that turned crystalline from ethylacetate.

Yield after recrystallizing once: 78% of theory.

M.p. 120°–122° C.

The product was identical to that produced according to Example 5.

EXAMPLE 10

Production of 4-(chloronaphthoxy<2>)-nitrobenzene by chlorinating 4-(β-naphthoxy)-nitrobenzene The procedure of Example 7 was followed. Instead of the 4-(α-naphthoxy)-3-chloronitrobenzene, the same molar quantity of 4-(β-naphthoxy)-nitrobenzene was used.

Crude yield: 95% of theory.

Recrystallization of the crude product that turned crystalline from di-isopropyl ether.

Yield after recrystallizing once: 73% of theory.

M.p. 111°–112° C.

The product was identical to that produced according to Example 6.

EXAMPLE 11

Production of 4-(bromonaphthoxy<1>)-nitrobenzene by brominating 4-(α-naphthoxy)-nitrobenzene A solution of 18 g (0.11 mol) of bromine in 50 ml of glacial acetic acid was added dropwise to a warm solution of 70° C. consisting of 26.5 g (0.10 mol) of 4-(α-naphthoxy)-nitrobenzene in 600 ml of glacial acetic acid, to which a little iron powder was added while stirring. After the addition was complete, the solution was stirred for 15 hours at 25°–30° C. Afterwards, the reaction solution was evaporated to dryness in vacuo. The residue was dissolved in toluene. The solution thus obtained was extracted with water several times. Subsequently, the solution was evaporated to dryness in vacuo.

Crude yield: 33.5 g (0.097 mol), 97% of theory.

The product, oily first, turned slowly crystalline. It was then recrystallized from di-isopropyl ether.

Yield after recrystallizing once: 24.5 g (0.71 mol), 71% of theory.

M.p. 71°–72° C.

(Bromine in 2- or 4-position of the naphthalene group; probably a mixture of both isomers was present).

EXAMPLE 12

Production of 4-(bromonaphthoxy<1>)-3-chloro-nitrobenzene by bromination of 4-(α-naphthoxy)-3-chloro-nitrobenzene The procedure of Example 11 was followed. However, instead of 4-(α-naphthoxy)-nitrobenzene, the same molar quantity of 4-(α-naphthoxy)-3-chloro-nitrobenzene was used.

Crude yield: 97% of theory.

Purification by suspension in a small amount of di-isopropylether.

Pure yield: 66% of theory.

M.p. 153°–155°.

EXAMPLE 13

Production of 4-(bromonaphthoxy<2>)-nitrobenzene by brominating 4-(α-naphthoxy)-nitrobenzene The procedure of Example 11 was followed. Instead of the 4-(α-naphthoxy)-nitrobenzene, an equal quantity of 4-(β-naphthoxy)-nitrobenzene was employed.

Crude yield: 97% of theory.

Purification of the hot toluene solution of the crude product with silicagel and subsequent recrystallization from di-isopropyl ether.

Pure yield: 68% of theory. M.p. 131°–133° C.

EXAMPLE 14

Production of 4-(bromonaphthoxy<2>)-3-chloro-nitrobenzene by brominating 4-(β-naphthoxy)-3-chloro-nitrobenzene The procedure of Example 11 was followed, with the exception that instead of the 4-(α-naphthoxy)-nitrobenzene, the same molar quantity of 4-(β-naphthoxy)-3-chloro-nitrobenzene was employed.

Crude yield: 96%—Purification as in Example 13.

Pure yield: 57% of theory.

M.p. 105°–107° C.

EXAMPLE 15

Production of 4-(2,4-dichloronaphthoxy 1)-3-chloro-nitrobenzene by chlorinating 4-(α-naphthoxy)-3-chloro-nitrobenzene Into a warm solution of 50° C. consisting of 30 g (0.10 mol) of 4-(α-naphthoxy)-3-chloro-nitrobenzene and 8.2 g (0.10 mol) of sodium acetate, chlorine was introduced under addition of 0.5 g of iron (III)-chloride, while stirring, until the reaction mixture took up 14.2 g (0.10 mol) of the chlorine. Then, stirring was continued for 15 minutes at 50° C. Subsequently, undissolved substance was recovered by suction filtration and the filtrate was evaporated in vacuo to the residue, which was dissolved in di-isopropyl ether. The solution was extracted several times with water, dried with magnesium sulfate, and then evaporated to the residue. The residue thus treated was dissolved in boiling benzene (boiling range 80° to 110° C.). During cooling off of the solution, a resin precipitated from the solution; then, the benzine solution was decanted. The product slowly crystallized out of the latter, i.e. from the benzine solution. The product was recovered by suction filtration and washed with benzine.

Yield: 12.4 g (0.041 mol), 41% of theory.
M.p. 121°-123° C.

All purified nitro compounds were analyzed. The C-, H-, N-, and, optionally, halogen values coincided in all cases with the theoretical values.

In addition, NMR-spectrums were made of these purified products. They also coincided with the indicated structures.

B. Anilines

EXAMPLE 16

4-(α-Naphthoxy)-aniline

A mixture of 1.5 liters of water, 40 ml of glacial acetic acid and 1.0 mol of 4-(α-naphthoxy)-nitrobenzene was heated to boiling while stirring. After the boiling temperature had been reached, 200 g of iron powder were added in small portions. When the addition was finished, it was refluxed for 6 hours, while stirring.

Then, the reaction mixture was allowed to cool off to room temperature. During such cooling, the components indissoluble in water separated. After several hours the supernatant, clear aqueous phase was cautiously decanted. To the remaining mixture 1.5 liters of acetone were added to dissolve the organic components. Undissolved particles were removed by suction filtration and washed again with acetone. After the filtrates were united, most of the acetone was distilled off. The distillation was interrupted as soon as the temperature of the steam was 95° C. The heterogeneous residue was stirred—after cooling off—with 1 liter of ethylene chloride until two liquid phases remained. These were separated, and the aqueous phase was extracted once more with ethylene chloride. The organic phases were united, dried with magnesium sulfate, and evaporated to the residue. An oily crude product remained, which was distilled under oil pump vacuum. The main distillate fraction crystallized slowly.

Crude yield: 220 g (0.936 mol); 93% of theory.
Pure yield: 195 g (0.830 mol); 83% of theory.
Boiling point: 181°-186° C.; 0.6-0.7 mbar.
M.p. 49°-50° C.

EXAMPLE 17

4-(β-Naphthoxy)-aniline

For reduction of the 4-(β-naphthoxy)-nitrobenzene, the procedure of Example 16 was followed (one quarter of the batch described there). During distillation of the crude product, the preliminary distillate fractions comprised some hexametapol and p-chloroaniline. The main distillate fraction became crystalline.

Pure yield: 41 g (0.174 mol) 70% of theory over both steps.
Boiling point: 194°-196° C./0.7 mbar.
M.p. 113°-115° C.

EXAMPLE 18

4-(α-Naphthoxy)-3-chloroaniline

The procedure of Example 16 was followed, starting from 4-(α-naphthoxy)-3-chloro-nitrobenzene (one quarter of the batch described there). During distillation of the crude product, the preliminary distillate fractions comprised some hexametapol and 3,4-dichloroaniline. Also, the main distillate fraction remained oily in a highly viscous form after a long time.

Pure yield: 50.4 g (0.187 mol) 75% of theory over both steps.
B.p. 193°-197° C./0.3 mbar.

Further anilines were produced in analogous fashion:

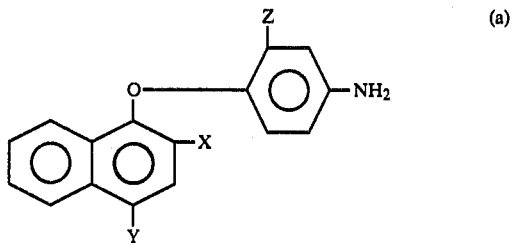

(a)

| Ex. | X  | Y  | Z  | M.p.       | B.p. |
|-----|----|----|----|------------|------|
| 19* | H  | Cl | H  |            |      |
| 20* | H  | Cl | Cl | 98-100° C. |      |
| 21* | H  | Br | H  |            |      |
| 22* | H  | Br | Cl | 92-94° C.  |      |
| 23  | Cl | Cl | Cl |            |      |

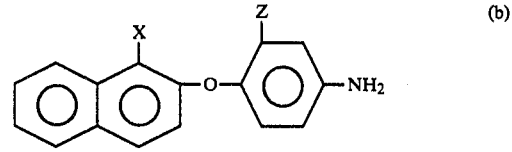

(b)

| Ex. | X  | Z  | M.p.       | b.p.              |
|-----|----|----|------------|-------------------|
| 24  | H  | Cl | 70-71° C.  | approx. 195° C./  |
| 25  | Cl | H  | 91-93° C.  | 0.13 mbar         |
| 26  | Cl | Cl | 90-92° C.  |                   |
| 27  | Br | H  | 94-96° C.  |                   |
| 28  | Br | Cl | 100-102° C.|                   |

*It is possible that the products partly comprise the corresponding isomers with X equalling halogen and Y equalling H.

C. Final products of formula

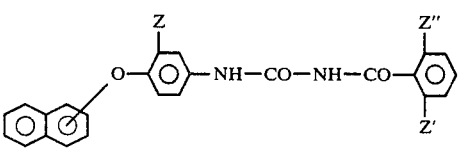

EXAMPLE 29

N-[4-(α-naphthoxy)-phenyl]-N'-(2-chloro-benzoyl)-urea

To a solution of 4.7 g (0.020 mol) of 4-(α-naphthoxy)-aniline in 100 ml of absolute toluene were added 3.65 g (0.020 mol) of o-chlorobenzoyl isocyanate. The reaction solution thus obtained was stirred at room temperature for 15 hours. During this time the product crystallized out. It was removed by suction filtration, washed with toluene, and dried.

Yield: 7.9 g (0.019 mol), 95% of theory.
M.p. 219°–221° C.

The urea derivatives mentioned in the following were processed in the same manner, using the same molar quantities of the corresponding naphthoxyanilines and the correspondingly substituted benzoyl isocyanates. In doing so, yields of 85 to 95% of theory were obtained.

(a) N-[4-(α-naphthoxy)-3-chloro-phenyl]-N'-(2-chloro-benzoyl)-urea; M.p. 221°–223° C.
(b) N-[4-(α-naphthoxy)-phenyl]-N'-(2,6-dichloro-benzoyl)-urea; M.p. 205°–208° C.
(c) N-[-(β-naphthoxy)-phenyl]-N'-(2,6-dichloro-benzoyl)-urea; M.p. 217°–220° C.
(d) N-[4-(α-naphthoxy)-phenyl]-N'-(2,6-difluoro-benzoyl)-urea; M.p. 215°–218° C.
(e) N-[4-(β-naphthoxy)-phenyl]-N'-(2,6-difluoro-benzoyl)-urea; M.p. 219°–222° C.
(f) N-[4-(α-naphthoxy)-3-chloro-phenyl]-N'-(2,6-difluoro-benzoyl)-urea; M.p. 229°–232° C.
(g) N-[4-(α-naphthoxy)-phenyl]-N'-(2-chloro-6-fluoro-benzoyl)-urea; M.p. 209°–211° C.
(h) N-[4-(β-naphthoxy)-phenyl]-N'-(2-chloro-6-fluoro-benzoyl)-urea; M.p. 206°–208° C.
(i) N-[4-(α-naphthoxy)-3-chloro-phenyl]-N'-(2-chloro-6-fluoro-benzoyl)-urea; M.p. 242°–245° C.

EXAMPLE 30

N-[4-(α-Naphthoxy)-phenyl]-N'-(2,6-dichloro-benzoyl)-urea

First Step
Production of the Isocyanate

Into a solution of 23.5 g (0.10 mol) of 4-(α-naphthoxy)-aniline in 200 ml of dioxan, hydrogen chloride was introduced while stirring at room temperature until no hydrochloride precipitated any more. After the mixture thus obtained was cooled to 5°–10° C., 15 g of phosgene were introduced into the mixture while stirring intensely. After the introduction was finished, the mixture was stirred for three hours at 25° C., then for one hour at 50° C., and finally another hour at 95° to 100° C. The result was a clear solution. Then, excess phosgene was expelled at 95° C. by introducing nitrogen. Subsequently, the solvent was distilled off in vacuo. The oily product remained. Yield: 26 g (0.995 mol) of 4-(α-naphthoxy)-phenylisocyanate (practically quantitative yield).

Second step
Production of the Urea

An amount of 9.5 g (0.50 mol) of 2,6-dichloro-benzoylamide and of 2 ml of triethylamine was added to a solution of 13.1 g (0.050 mol) of 4-(α-naphthoxy)-phenyl isocyanate in 100 ml of dioxan. The mixture thus obtained was refluxed for 15 hours while stirring. Then the solvent was distilled off, and the residue was triturated with 100 ml of toluene. The product remained undissolved in crystalline condition. It was removed by suction filtration and dried.

Yield: 19.4 g (86% of theory).
M.p. 194°–198° C.

The second step has also been performed as follows:
One gram of sodium was added to a solution of 13.1 g (0.05 mol) of 4-(α-naphthoxy)-phenyl isocyanate and 9.5 g (0.050 mol) of 2,6-dichloro-benzoylamide in 50 ml of pyridine. The mixture thus obtained was heated to 100° C. for 24 hours. Then, it was allowed to cool to room temperature, and the cooled reaction mixture was stirred into a mixture of 250 g of ice and 250 ml of conc. hydrochloric acid. The precipitate crystallizing out when doing so was removed by suction filtration and it was washed first with water and then with ethanol.

Yield: 18.8 g (0.0417 mol); 83% of theory.
M.p. 196°–200° C.

There were obtained analogously:

(a) N-[4-(α-naphthoxy)-phenyl]-N'-(2-chlorobenzoyl)-urea; M.p. 211°–215° C.
(b) N-[4-(α-naphthoxy)-3-chloro-phenyl]-N'-(2-chlorobenzoyl)-urea; M.p. 214°–218° C.
(c) N-[4-(β-naphthoxy)-phenyl]-N'-(2,6-dichloro-benzoyl)-urea; M.p. 210°–214° C.
(d) N-[4-(α-naphthoxy)-phenyl]-N'-(2,6-difluoro-benzoyl)-urea; M.p. 211°–214° C.
(e) N-[4-(β-naphthoxy)-phenyl]-N'-(2,6-difluoro-benzoyl)-urea; M.p. 213°–217° C.
(f) N-[4-(α-naphthoxy)-3-chloro-phenyl]-N'-(2,6-difluoro-benzoyl)-urea; M.p. 222°–226° C.
(g) N-[4-(α-naphthoxy)-phenyl]-N'-(2,6-chloro-6-fluoro-benzoyl)-urea; M.p. 205°–208° C.
(h) N-[4-(β-naphthoxy)-phenyl]-N'-(2-chloro-6-fluoro-benzoyl)-urea; M.p. 201°–204° C.
(i) N-[4-(α-naphthoxy)-3-chloro-phenyl]-N'-(2-chloro-6-fluoro-benzoyl)-urea; M.p. 235°–239° C.

EXAMPLE 31

N-[4-(α-Naphthoxy)-phenyl]-N'-(2,6-dichlorobenzoyl)-urea

The starting compound N-(2,6-dichloro-benzoyl)-O-ethyl-urethane was prepared by reacting a suspension of the sodium salt of 2,6-dichloro-benzamide in dioxan with ethylchloroformate. By treating the crude product with toluene or xylene, unreacted 2,6-dichlorobenzamide was separated, as the urethane is easily soluble in these solvents; however, the amide is only difficulty soluble. The solution of 4.70 g (0.020 mol) of 4-(α-naphthoxy)-aniline and 5.75 g (0.022 mol) of N-(2,6-dichlorobenzoyl)-O-ethyl-urethane in 60 ml of absolute xylene was heated for adding xylene afterwards in a distillation apparatus with short distillating column and dropping funnel, so that the alcohol formed and the solvent distilled over very slowly. During the distillation, as much xylene as was dropped into the reaction mixture as distillate distilled over. The still temperature increased from 80° C. in the beginning to 137° C. After distillation for five hours, the addition of solvents was finished and the solvent of the reaction mixture was distilled off without column, at the end in vacuo. There remained 9.6 g of a mixture of substances, the main component of which was N-[4-(α-naphthoxy)-phenyl]-N'-(2,6-dichloro-benzoyl)-urea.

D. Final products of the formula

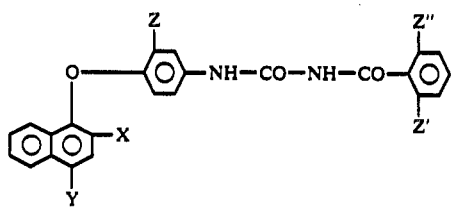

The compounds set forth in the following table were prepared according to procedures analogous to those described in Section C:

TABLE II

| Ex. | Y | X | Z | Z' | Z" | m.p. [°C.] |
|---|---|---|---|---|---|---|
| 32* | Cl | H | H | Cl | Cl | 240–242 |
| 33* | Cl | H | H | F | F | 213–215 |
| 34* | Cl | H | H | Cl | F | 220–222 |
| 35* | Cl | H | H | Cl | H | 221–223 |
| 36* | Cl | H | Cl | Cl | Cl | 250–252 |
| 37* | Cl | H | Cl | F | F | 232–234 |
| 38* | Cl | H | Cl | Cl | F | 246–248 |
| 39* | Cl | H | Cl | Cl | H | 214–216 |
| 40* | Br | H | H | Cl | Cl | 245–247 |
| 41* | Br | H | H | F | F | 214–215 |
| 42* | Br | H | H | Cl | F | 227–229 |
| 43* | Br | H | H | Cl | H | 216–218 |
| 44* | Br | H | Cl | Cl | Cl | 245–247 |
| 45* | Br | H | Cl | F | F | 228–230 |
| 46* | Br | H | Cl | Cl | F | 233–236 |
| 47* | Br | H | Cl | Cl | H | 219–222 |
| 48 | Cl | Cl | Cl | Cl | Cl | 247–249 |
| 49 | Cl | Cl | Cl | F | F | 255–257 |
| 50 | Cl | Cl | Cl | Cl | F | 251–253 |
| 51 | Cl | Cl | Cl | Cl | H | 242–245 |

*These compounds may partially comprise isomers wherein Y is hydrogen and X is halogen.

E. Final products of formula

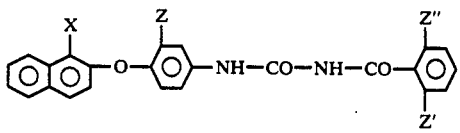

The compounds set forth in the following table were prepared according to procedures analogous to those described in Section C:

TABLE III

| Ex. | X | Z | Z' | Z" | m.p. (°C.) |
|---|---|---|---|---|---|
| 52 | Cl | H | Cl | Cl | 227–229 |
| 53 | Cl | H | F | F | 237–239 |
| 54 | Cl | H | Cl | F | 235–238 |
| 55 | Cl | H | Cl | H | 227–229 |
| 56 | Cl | Cl | Cl | Cl | 253–255 |
| 57 | Cl | Cl | F | F | 244–246 |
| 58 | Cl | Cl | Cl | F | 255–257 |
| 59 | Cl | Cl | Cl | H | 230–232 |
| 60 | Br | H | Cl | Cl | 235–237 |
| 61 | Br | H | F | F | 234–236 |
| 62 | Br | H | Cl | F | 233–235 |
| 63 | Br | H | Cl | H | 225–227 |
| 64 | Br | Cl | Cl | Cl | 251–255 |
| 65 | Br | Cl | F | F | 243–245 |
| 66 | Br | Cl | Cl | F | 246–248 |
| 67 | Br | Cl | Cl | H | 230–233 |

F. Compound of Formula A, wherein A represents group IIa or IIb.

EXAMPLE 68

N-(4-naphthylmercapto-phenyl)-N'-(2,6-dichloro-benzoyl)-urea (a) 4-nitrobenzene sulfenyl chloride Chlorine was introduced into a suspension of 30.8 g (0.10 mol) of di-(4-nitrophenyl)-disulfide in 200 ml of chloroform, while stirring, at a temperature of 25° to 30° C. until a clear solution was obtained and no more chlorine was taken up. Then stirring was continued for 3 hours at 40° to 45° C. Then, the solvent was distilled off in vacuo at a bath temperature of a maximum of 50° C. The remainder comprised oily 4-nitrobenzene sulfenyl chloride.

(b) 4-nitrophenyl-naphthyl-thioether

The crude 4-nitrobenzene sulfenyl chloride (38 g of product from the previous step) was added to 200 g of molten naphthalene at 80° C. Subsequently, 0.5 g of Fe(III)-chloride were added. Then, while stirring, the combination was heated to such a high temperature (in this case to ~95° C.) that hydrogen chloride was clearly liberated. After the gas liberation ceased, the reaction mass was stirred for a further one to two hours at approx. 105° C.

Afterwards, the excess naphthalene was distilled off in a water-jet vacuum apparatus. The distillation residue was dissolved in 300 ml of ethylene chloride, and this solution was extracted twice with water. After addition of 0.5 liters of water, the organic phase was distilled in vacuo, until the distillate remained clear. The residue was again dissolved in 300 ml of ethylene chloride; the remaining water was separated. Then, the solvent was distilled off in vacuo. Subsequently, the residue was boiled with 1000 ml of benzine (boiling temperature: 40° to 80° C.), while stirring. Then, undissolved, solid components were filtered off and treated twice, each time with 1000 ml of benzine. Finally, the di-(4-nitrophenyl)-disulfide which formed as a side-product remained undissolved and was isolated by filtration. The filtrates were united and evaporated. The oily product remained as residue.

Yield: 31.3 g (0.111 mol) of 4-nitrophenyl-naphthyl-thioether corresponding to 55.5% of theory referred to di-(4-nitrophenyl)disulfide employed in step (a).

regained: 12.5 g (0.040 mol) of di-(4-nitrophenyl)disulfide corresponding to ~40% of the quantity employed in step (a).

(c) 4-naphthylmercapto-aniline

An amount of 34 g of iron powder was added, while stirring, to a mixture of 31.0 g (0.11 mol) of 4-nitrophenyl-naphthyl thioether (product of the preceding step), 500 ml of water, and 2 ml of acetic acid. Subsequently, the mixture thus obtained was stirred well at 95°–100° C. for 5 hours. Under these conditions, the mixture assumed a dark brown color.

Afterwards, the reaction mixture was allowed to cool off to 60° C. When this temperature was reached, 200 ml of ethylene chloride and 10 g of kieselguhr were added. Then the mixture thus obtained was stirred intensely for 5 minutes. Then, the solid components were removed by suction filtration. The filtrate separated into 2 phases. The organic phase was isolated, extracted once with 50 ml of water and evaporated in vacuo to the residue. The oily product remained.

Yield: 25.7 g (0.102 mol) of 4-naphthylmercapto-aniline, corresponding to 93% of theory referred to the employed nitro compound.

(d) N-(4-naphthylmercapto-phenyl)-N'-(2,6-dichlorobenzoyl)-urea

To a solution of 2.51 g (10 mmol) of 4-(naphthylmercapto)-aniline in 20 ml of toluene was added at room temperature a solution of 2.4 g (11 mmol) of 2,6-dichlorobenzoyl-isocyanate in 10 ml of toluene. As a result, the reaction mixture warmed up to ~30° C. Then it was allowed to remain at room temperature for 15 hours. During this time part of the product crystallized out. The crystallized product was removed by suction filtration and dried. The filtration was evaporated in vacuo to the residue. Yield of crystallized product: 3.3 g (71% of theory) m.p. 207°–209° C.

According to the results of the elementary analysis and the NMR-spectrum, the desired product was present in pure form (or as mixture of isomers of an α- and β-naphthyl compound).

From the mother liquor 1.2 g of residue (crude product were obtained.

M.p. 166°–170° C.

According to the elementary analysis and the NMR-spectrum, this substance consists preponderantly of the desired product.

As an alternative to step (d) the following reaction steps were practicable:

(e) 4-naphthylmercapto-phenyl-isocyanate

Into a solution of 25.1 g (0.10 mol) of 4-naphthylmercapto aniline (product of step (c)) in 200 ml of dioxan, hydrogen chloride was introduced while stirring at room temperature, until no further hydrochloride was precipitated. Subsequently, there were introduced into the mixture thus obtained, after cooling to 5°–10° C., while stirring intensely, 15 g of phosgene. After the introduction was finished, the reaction mixture was heated to approx. 25° C. and stirred for 3 hours at this temperature. During this time a clear solution resulted. This was stirred for one hour at 50° C. and then for another hour at 95°–100° C. Then excess phosgene was expelled by introducing nitrogen at ·95° C. Then, the solvent was distilled off in vacuo. The oily product remained.

Yield: 27.5 g (0.993 mol) of 4-naphthylmercapto-phenylisocyanate, practically a quantitative yield.

(f) N-(4-naphthylmercapto-phenyl)-N'-(2,6-dichlorobenzoyl)-urea

To a solution of 11.0 g (40 mmol) of isocyanate (product of step (e)) in 100 ml of dioxan were added 7.6 g (40 mmol) of 2,6-dichlorobenzoylamide and 2 ml of triethylamino. The mixture thus obtained was refluxed for 15 hours. Then, the solvent was distilled off in vacuo and the residue was dissolved in a mixture of 100 ml of ethylene chloride and 100 ml of water. Then the aqueous phase was separated and the organic phase was extracted twice, each time with 100 ml of water. Subsequently, the organic phase was dried with magnesium sulfate. Then, the solvent was distilled off in vacuo. The residue, oily in the beginning, became crystalline after triturating it with water. The crystals were removed by suction filtration and dried in the vacuum desiccator by means of concentrated sulfuric acid.

Yield: 17.8 g (28.2 mmol) of N-(4-naphthylmercapto-phenyl)-N'-(2,6-dichlorobenzoyl)-urea corresponding to 95% of theory referred to the isocyanate used.

M.p. 188°–190° C.

EXAMPLE 69

N-(4-Tolylmercapto-phenyl)-N'-(2,6-dichlorobenzoyl) urea (a) 4-nitrophenyl-tolyl-thioether Crude p-nitrobenzene sulfenyl chloride (38 g) was dissolved in 200 ml of toluene. After addition of 0.5 g of iron (III) chloride, the solution was heated while stirring until hydrogen chloride was clearly liberated (in this case from ~70°–80° C.). After liberation ceased, stirring was continued at an approx. 10° higher temperature. Afterwards, the solution was allowed to cool off to ~30° C. and extracted thrice, each time with 100 ml of water. Then, the organic phase was evaporated in vacuo to the residue. This residue was boiled with 500 ml of benzine (range of boiling temperature 40°–80° C.). Solid components still present afterwards were filtered off and treated twice again with separate portions of 500 ml of benzine. Di-(4-nitrophenyl) disulfide remained undissolved as side-product. The filtrates were united and evaporated to the residue.

The oily product remained.

Yield: 25.0 g (0.102 mol) of 4-nitrophenyl-tolyl-thioether; regained: 13 g (0.042 mol) of di-(4-nitrophenyl)-disulfide.

(b) 4-tolylmercapto-aniline

Batch: 24.5 g (0.10 mol) p-nitrophenyl-tolyl-thioether (product of the preceding step).

Method of working as described in Example 68(c).

Yield: 20.4 g (0.095 mol) of 4-tolylmercapto-aniline, corresponding to 95% of theory (based on employed nitro compound).

(c) N-(4-tolylmercapto-phenyl)-N'-(2,6-dichlorobenzoyl)-urea

Batch: 2.15 g (10 mmol) of 4-tolylmercapto-aniline (product of the preceding step).

Method of working as described in Example 68(d).

Yield of product crystallized out: 2.13 g (4.9 mmol; 49% of theory).

M.p. 189°–203° C.

According to the results of the elementary analysis and the NMR-spectrum, a pure mixture of isomers was present (position of the methyl group of the tolyl group uncertain).

Yield of cure product from the mother liquor: 2.0 g. M.p. 148°–152° C.

In line with the results of the elementary analysis and the NMR-spectrum, this product was a largely pure mixture of isomers.

The following was obtained in analogous fashion: n-[4-tolylmercapto-3-chlorophenyl]-N'-(2,6-dichlorobenzoyl)-urea, m.p. 192°–195° C.

The following compounds were obtained according to analogous procedures:

TABLE IV

Formula

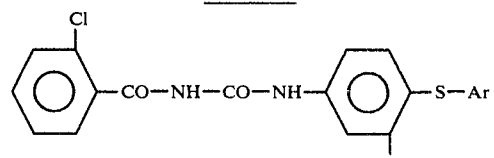

| Example | Z | Ar | m.p.(°C.) |
|---------|---|-----|-----------|
| 70 | H | ⌬—CH₃ | 170–172 |

TABLE IV-continued

Formula

| Example | Z | Ar | m.p.(°C.) |
|---|---|---|---|
| 71 | Cl |  | 186–189 |
| 72 | Cl |  | 227–230 |

TABLE V

Formula

| Example | Z | Ar | m.p.(°C.) |
|---|---|---|---|
| 73 | H |  | 186–188 |
| 74 | H | 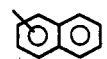 | 213–215 |
| 75 | Cl |  | 197–199 |
| 76 | Cl | 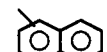 | 236–239 |

TABLE VI

Formula

| Example | Z | Ar | m.p. (°C) |
|---|---|---|---|
| 77 | H |  | 138–139 |
| 78 | H | | 197–198 |
| 79 | Cl | | 201–204 |
| 80 | Cl | | 245–247 |

All the compounds mentioned in Tables IV to VI have been characterized by elemantary analyses and NMR-spectrums.

A preferred compound of the -S-Ar type is N-(naphthylmercaptophenyl)-N'-(2-chlor-6-fluorbenzoyl)-urea.

The nitro compounds used as starting materials of formula

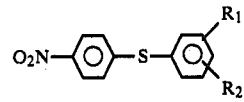

have been set forth in the following table:

TABLE VII

| Ex. | $R_1$ | $R_2$ | Position of $R_1$ and $R_2$ towards each other | m.p. or consistency of crude products |
|---|---|---|---|---|
| 81* | —H | —CH₃ | — | oil |
| 82* | —H | —C₂H₅ | — | oil |
| 83* | —CH₃ | —CH₃ | m | oil |
| 84* | —CH₃ | —CH₃ | p | oil |
| 85* | —H | —CH(CH₃)₂ | — | oil |
| 86* | —H | —O—C₂H₅ | — | 86–88° C. |
| 87* | —CH₃ | —OC₂H₅ | m | 79–81° C. |
| 88* | —H | —CH(CH₃)—C₂H₅ | — | oil |
| 89* | —H | —CH₂—CH(CH₃)₂ | — | oil |
| 90* | —CH=CH—CH=CH— | | o | oil |
| 91* | —H | —O—(CH₂)₃—CH₃ | — | 73–75° C. |
| 92* | —CH₃ | —O—(CH₂)₃—CH₃ | m | 57–59° C. |
| 93* | —CH₃ | —OCH₃ | m | 57–59° C. |

*Mixture of isomers with respect to position of $R_1/R_2$ towards S.

Similarly the starting materials of formula

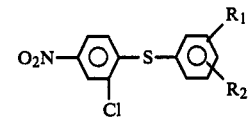

have been set forth in the following table:

TABLE VIII

| Ex. | $R_1$ | $R_2$ | Position of $R_1$ and $R_2$ towards each other | M.p. or consistency of crude products |
|---|---|---|---|---|
| 94* | —H— | —CH₃ | — | oil |
| 95* | —CH=CH—CH=CH— | | o | 81–83° C. |

*Mixture of isomers with respect to the position of $R_1/R_2$ towards S.

The preceding specific embodiments are illustrative of the practice of the invention. It is to be understood, however, that other expedients known to those skilled in the art, or disclosed herein, may be employed without departing from the spirit of the invention or the scope of the appended claims.

We claim:

1. A compound of the formula

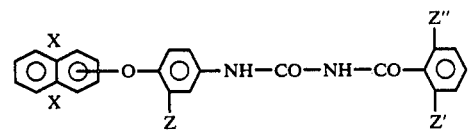

wherein
X and Y are each independently hydrogen, chlorine or bromine;
Z is hydrogen or chlorine;
Z' is chlorine or fluorine; and
Z'' is hydrogen, chlorine or fluorine.

2. A compound of claim 1, which is of the formula

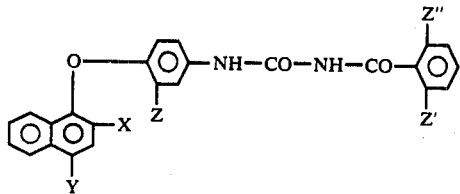

wherein
one of X and Y is chlorine and the other is hydrogen, or both are hydrogen, and
Z, Z' and Z" have the meanings defined in claim 1.

3. A compound of claim 2, where one of X and Y is bromine and the other is hydrogen.

4. The compound of claim 1 which is N-[4-(α-naphthoxy)-phenyl]-N'-(2-chlorobenzoyl)-urea.

5. The compound of claim 1 which is N-[4-(α-naphthoxy)-phenyl]-N'-(2-chloro-6-fluorobenzoyl)-urea.

6. The compound of claim 1 which is N-[4-(β-naphthoxy)-phenyl]-N'-(2-chloro-6-fluorobenzoyl)-urea.

7. A pesticidal composition consisting essentially of an inert carrier and an effective insecticidal or acaricidal amount of a compound of claim 1.

8. The method of killing insects or acarids, which comprises contacting the same with an effective insecticidal or acaricidal amount of a compound of claim 1.

* * * * *

UNITED STATES PATENT AND TRADEMARK OFFICE
CERTIFICATE OF CORRECTION

PATENT NO. : 4,275,077
DATED : June 23, 1981
INVENTOR(S) : HEINZ-MANFRED BECHER ET AL.

It is certified that error appears in the above—identified patent and that said Letters Patent is hereby corrected as shown below:

Column 2, line 25: "benzoy" should read -- benzoyl --.

line 26: "lurethane" should read -- urethane --.

Column 11, line 44: "naphthox-" should read -- naphthoxy)- --.

line 45: Delete "y)-".

Column 15, line 41: ".95°C." should read -- ∿95°C. --

Column 17, Table IV, Example 71: The structural formula

Table IV, Example 72: The structural formula

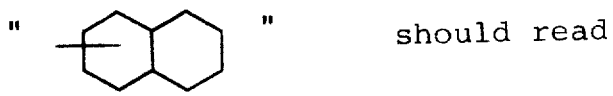 should read

-- 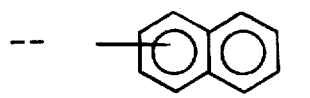 -- .

UNITED STATES PATENT AND TRADEMARK OFFICE
CERTIFICATE OF CORRECTION

PATENT NO. : 4,275,077  PAGE 2 of 2
DATED : June 23, 1981
INVENTOR(S) : HEINZ-MANFRED BECHER ET AL.

It is certified that error appears in the above—identified patent and that said Letters Patent is hereby corrected as shown below:

Column 18, Claim 1: The portion of the structural formula which reads

" 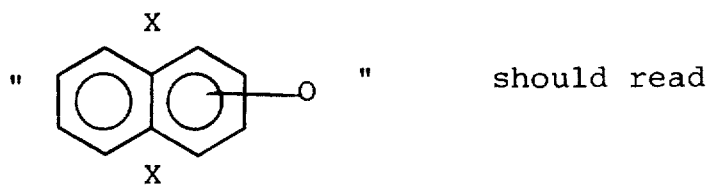 " should read

-- 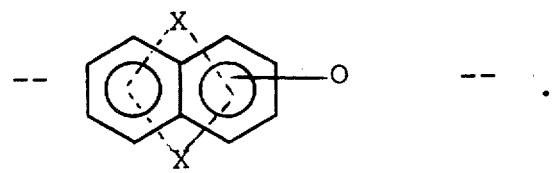 -- .

Signed and Sealed this

Fifteenth Day of September 1981

[SEAL]

Attest:

GERALD J. MOSSINGHOFF

Attesting Officer   Commissioner of Patents and Trademarks